United States Patent
Hammon et al.

(10) Patent No.: US 9,925,526 B2
(45) Date of Patent: Mar. 27, 2018

(54) OXIDATION CATALYST WITH SADDLE-SHAPED SUPPORT BODY

(71) Applicant: BASF SE, Ludwigshafen (DE)

(72) Inventors: Ulrich Hammon, Mannheim (DE); Cathrin Alexandra Welker-Nieuwoudt, Birkenheide (DE); Josef Macht, Antwerp (BE); Christian Walsdorff, Ludwigshafen (DE); Cornelia Katharina Dobner, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 42 days.

(21) Appl. No.: 14/633,433

(22) Filed: Feb. 27, 2015

(65) Prior Publication Data

US 2015/0246343 A1 Sep. 3, 2015

Related U.S. Application Data

(60) Provisional application No. 61/945,845, filed on Feb. 28, 2014.

(30) Foreign Application Priority Data

Feb. 28, 2014 (DE) .................... 10 2014 203 725 U

(51) Int. Cl.
*B01J 23/888* (2006.01)
*B01J 35/00* (2006.01)
(Continued)

(52) U.S. Cl.
CPC ......... *B01J 23/8885* (2013.01); *B01J 23/002* (2013.01); *B01J 23/007* (2013.01);
(Continued)

(58) Field of Classification Search
CPC .. B01J 23/8885; B01J 23/002; B01J 23/8877; B01J 23/007; B01J 23/70; B01J 35/1009;
(Continued)

(56) References Cited

U.S. PATENT DOCUMENTS

| 3,147,084 A | 9/1964 | Franzen et al. |
| 3,911,039 A | 10/1975 | Grasselli et al. |

(Continued)

FOREIGN PATENT DOCUMENTS

| AT | 333 704 | 12/1976 |
| DE | 522572 | 4/1931 |

(Continued)

OTHER PUBLICATIONS

International Search Report and Written Opinion of the International Searching Authority dated Jun. 5, 2015 in PCT/EP2015/053897.

(Continued)

*Primary Examiner* — Anthony J Zimmer
(74) *Attorney, Agent, or Firm* — Oblon, McClelland, Maier & Neustadt, L.L.P.

(57) ABSTRACT

The invention relates to an oxidation catalyst comprising at least one inorganic, oxidic or ceramic, shaped support body having a BET surface area of less than 0.5 m²/g, based on the support, which is at least partly coated with a catalytically active multielement oxide, the catalyst being precious metal-free and the shaped support body having the form of a saddle whose saddle surface is curved oppositely in the two principal directions, to a process for producing it, to its use in various catalytic gas phase oxidations, and to corresponding processes for catalytic gas phase oxidation.

13 Claims, 4 Drawing Sheets

(51) Int. Cl.

| | |
|---|---|
| *B01J 35/10* | (2006.01) |
| *B01J 37/00* | (2006.01) |
| *B01J 37/02* | (2006.01) |
| *C07C 5/48* | (2006.01) |
| *C07C 51/235* | (2006.01) |
| *B01J 23/00* | (2006.01) |
| *B01J 23/70* | (2006.01) |
| *B01J 23/887* | (2006.01) |
| *B01J 32/00* | (2006.01) |
| *C07C 51/31* | (2006.01) |
| *C07C 51/25* | (2006.01) |
| *C07D 307/89* | (2006.01) |

(52) U.S. Cl.
CPC ........... *B01J 23/70* (2013.01); *B01J 23/8877* (2013.01); *B01J 32/00* (2013.01); *B01J 35/0006* (2013.01); *B01J 35/1009* (2013.01); *B01J 37/0009* (2013.01); *B01J 37/0215* (2013.01); *C07C 5/48* (2013.01); *C07C 51/235* (2013.01); *C07C 51/252* (2013.01); *C07C 51/313* (2013.01); *C07D 307/89* (2013.01); *B01J 2219/30203* (2013.01); *B01J 2219/30475* (2013.01); *C07C 2523/888* (2013.01)

(58) Field of Classification Search
CPC .... B01J 2219/30475; B01J 2219/30203; B01J 37/0009; B01J 32/00; B01J 37/0215; B01J 35/0006; C07C 51/252; C07C 5/48; C07C 51/235; C07C 51/313; C07C 2523/888; C07C 307/89; C07D 307/89
See application file for complete search history.

(56) References Cited

U.S. PATENT DOCUMENTS

| | | | |
|---|---|---|---|
| 4,162,234 A | 7/1979 | Grasselli et al. | |
| 4,336,409 A | 6/1982 | Yamamoto et al. | |
| 4,423,281 A | 12/1983 | Yamamoto et al. | |
| 4,424,141 A | 1/1984 | Grasselli et al. | |
| 4,547,615 A | 10/1985 | Yamamoto | |
| 4,645,754 A | 2/1987 | Tamura et al. | |
| 5,677,261 A * | 10/1997 | Tenten | B01J 23/002 |
| | | | 502/311 |
| 5,792,719 A | 8/1998 | Eberle et al. | |
| 5,919,425 A | 7/1999 | Nguyen et al. | |
| 6,281,385 B1 | 8/2001 | Ruedinger et al. | |
| 6,293,979 B1 | 9/2001 | Choudhary et al. | |
| 6,989,454 B2 * | 1/2006 | Hibst | C07D 307/60 |
| | | | 549/262 |
| 2004/0171887 A1 * | 9/2004 | Berndt | B01J 23/002 |
| | | | 568/476 |
| 2011/0275856 A1 | 11/2011 | Karpov et al. | |
| 2012/0029214 A1 * | 2/2012 | Altwasser | B01J 23/22 |
| | | | 549/248 |

FOREIGN PATENT DOCUMENTS

| | | |
|---|---|---|
| DE | 2 201 528 | 11/1972 |
| DE | 24 40 329 A1 | 3/1975 |
| DE | 24 47 825 A1 | 8/1975 |
| DE | 25 30 959 A1 | 2/1976 |
| DE | 26 00 128 A1 | 7/1976 |
| DE | 28 30 765 A1 | 1/1980 |
| DE | 29 03 582 A1 | 8/1980 |
| DE | 29 09 671 A1 | 10/1980 |
| DE | 25 13 405 C2 | 10/1982 |
| DE | 40 06 935 A1 | 9/1991 |
| DE | 198 24 532 A1 | 12/1999 |
| DE | 199 27 624 A1 | 12/2000 |
| DE | 199 48 248 A1 | 4/2001 |
| DE | 103 60 057 A1 | 7/2004 |
| DE | 10 2005 010 645 A1 | 8/2005 |
| DE | 10 2011 079 035 A1 | 1/2013 |
| EP | 0 192 314 A2 | 8/1986 |
| EP | 0 218 766 A1 | 4/1987 |
| EP | 0 297 445 A2 | 1/1989 |
| EP | 0 383 224 A2 | 8/1990 |
| EP | 0 467 144 A1 | 1/1992 |
| EP | 0 714 700 A2 | 6/1996 |
| EP | 0 873 783 A1 | 10/1998 |
| EP | 0 966 324 B1 | 4/2003 |
| JP | 61021729 A * | 1/1986 |
| WO | WO 2005/030388 A1 | 4/2005 |
| WO | WO 2009/124945 A2 | 10/2009 |
| WO | WO 2009/124974 A2 | 10/2009 |
| WO | WO 2009/133065 A1 | 11/2009 |
| WO | WO 2011/134932 A1 | 11/2011 |
| WO | WO 2012/014154 A1 | 2/2012 |

OTHER PUBLICATIONS

Examination Report received in Singapore Application No. 11201607054V, dated Oct. 6, 2017.

* cited by examiner

OXIDATION CATALYST WITH SADDLE-SHAPED SUPPORT BODY

The invention relates to an oxidation catalyst, to a process for producing it, to its use in various catalytic gas phase oxidations, and to corresponding processes for catalytic gas phase oxidation.

Eggshell catalysts which comprise as the eggshell a multielement oxide which is catalytically active in oxidation reactions are known per se.

WO 2011/134932 discloses an eggshell catalyst consisting of a hollow-cylindrical shaped support body and also of an eggshell which is applied to the outer surface of the shaped support body and comprises catalytically active oxide composition, and also discloses a process for preparing acrylic acid by gas phase-catalytic oxidation of acrolein over a fixed catalyst bed that comprises the eggshell catalyst. In the working examples, selectivities for acrylic acid formation of up to 97.5% are achieved after 100 hours of operation.

Also known are oxidation catalysts which comprise a saddle body as their porous, inorganic, refractory support.

EP-A-0 218 766 describes a silver catalyst for producing ethylene oxide by catalytic vapor phase oxidation of ethylene with molecular oxygen. In the catalyst employed, silver and at least one accelerator selected from the group of alkali metals and alkali metal compounds are deposited on a porous inorganic refractory support which is designed as Intalox saddles or Berl saddles.

Likewise known from the catalytic reforming of hydrocarbons are catalysts in which the catalyst support has the form of a saddle (EP-A-0 192 314). The support consists of a calcined calcium aluminate cement composition. The catalyst supports have an overall surface area, determined by nitrogen adsorption, of 0.5 to 40 m²/g. The catalyst comprises preferably nickel and/or cobalt.

AT 333 704 describes a support of oxidation catalysts that is designed preferably as a saddle body and is based on alumina. The alumina is doped with 2 to 10 wt % of rare earth metals in the form of oxides. This catalyst support is again a porous catalyst support.

It is an object of the present invention to provide oxidation catalysts, especially for the oxidation of (meth)acrolein to (meth)acrylic acid, of o-xylene and/or naphthalene to phthalic anhydride, or of alkenes to alkadienes or aldehydes, that features improved selectivity and a lower pressure drop than the known catalysts and that also retains this low pressure drop over the course of the operating life.

The object is achieved in accordance with the invention by means of an oxidation catalyst comprising at least one inorganic, oxidic or ceramic, shaped support body having a BET surface area of less than 0.5 m²/g, based on the support, which is at least partly coated with a catalytically active multielement oxide, the catalyst being precious metal-free and the shaped support body having the form of a saddle whose saddle surface is curved oppositely in the two principal directions.

The known saddle-shaped oxidation catalysts are impregnated solid materials, which like customary catalyst supports have not too low a porosity, in order to be able to be coated by means of impregnating methods.

The shaped support bodies used in accordance with the invention, in contrast, have a very low BET surface area of less than 0.5 m²/g, and are substantially nonporous.

The oxidation catalyst used in accordance with the invention, furthermore, preferably has no internal volume, and so in the course of operation it experiences no or virtually no clogging with coke or coking residues. This as well allows the pressure loss to be kept low.

The object is also achieved by means of a process for producing an oxidation catalyst of this kind, in which the inorganic oxidic or ceramic support is coated with a powder of the multielement oxide, optionally with accompanying use of a binder.

The invention further relates to the use of an oxidation catalyst of this kind for the catalytic gas phase oxidation of propene to acrolein, of propene or acrolein to acrylic acid, of tert-butanol, isobutane, isobutene, or tert-butyl methyl ether to methacrolein, of methacrolein or isobutyraldehyde to methacrylic acid, of o-xylene and/or naphthalene to phthalic anhydride, or of alkenes to alkadienes.

The invention further relates to a process for preparing an $\alpha,\beta$-unsaturated carboxylic acid by gas phase oxidation of an $\alpha,\beta$-unsaturated aldehyde with molecular oxygen over a fixed catalyst bed which comprises a bed of a catalyst of the formulae (I) or (III) hereinafter.

The invention further relates to a process for preparing phthalic anhydride by gas phase oxidation of o-xylene and/or naphthalene with molecular oxygen over a fixed catalyst bed which comprises a bed of a catalyst as described hereinafter, based on vanadium oxide and titanium dioxide.

The invention further relates to a process for oxidatively dehydrogenating n-butenes to butadiene, in which an initial gas mixture comprising n-butenes is contacted with an oxygen-comprising gas, optionally mixed with additional inert gas or water vapor, in a fixed bed reactor at a temperature of 220 to 490° C. with a catalyst of the general formula (IV) arranged in a fixed catalyst bed.

Figure 1:
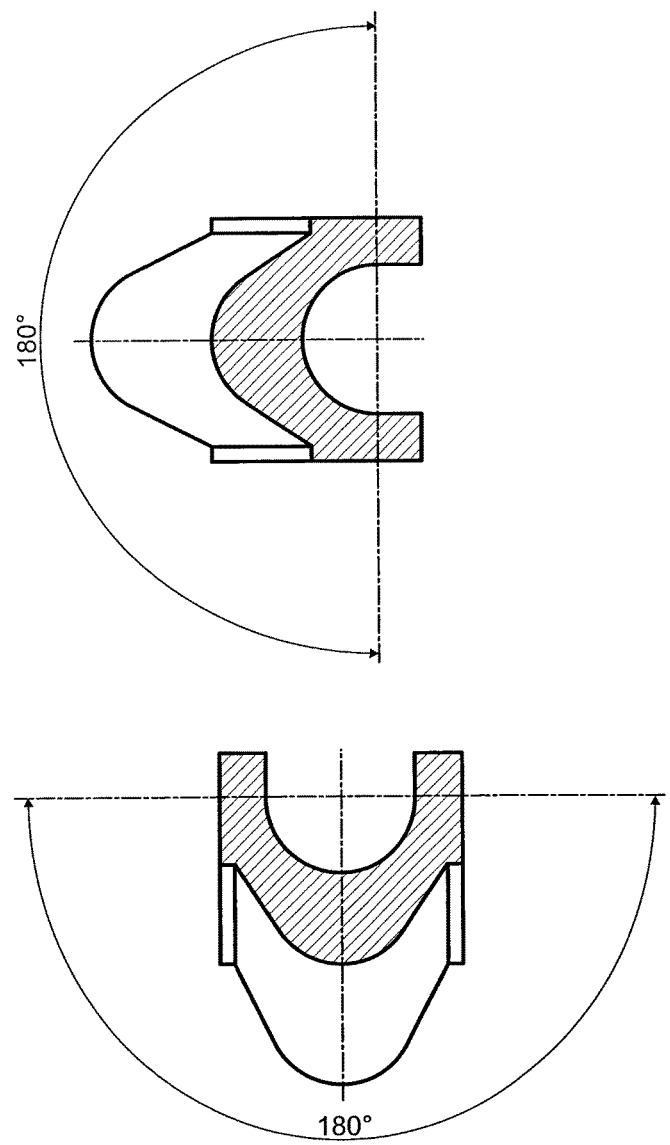
FIG. 1 shows a saddle suitable in accordance with the invention.

The oxidation catalysts of the invention are produced using inorganic, oxidic or ceramic, shaped support bodies which have a BET surface area of less than 0.5 m²/g, based on the support. The shaped support bodies have the form of a saddle whose saddle surface is curved oppositely in the two principal directions.

The inorganic, oxidic or ceramic, shaped support body is based on inorganic oxides.

According to Römpp Chemielexikon, 9th edition, ceramic materials are materials which are more than 30 vol % crystalline and are composed of inorganic and predominantly nonmetallic compounds or elements. They are produced according to the conventional methods of ceramics, or modern techniques, of glass-ceramic, oxide-ceramic or powder metallurgy, for example. In ceramics, in addition to oxides, it is also possible to use carbides, nitrides, silicides, and similar compounds as raw materials. In the course of their production, there is a solidification at high temperatures as a result of solid/solid reactions.

The shaped support body consists preferably of (refractory) inert material. "Inert" means that the material of the shaped support body does not alter substantially under the conditions of the gas phase oxidation, and has no catalytic activity, or at most negligible catalytic activity, as far as the gas phase oxidation is concerned, by comparison with the active composition that is applied. Inert material contemplated includes, in particular, alumina, silica, silicon carbide, zirconium dioxide, thorium dioxide, silicates such as clay, kaolin, steatite, pumice, aluminum silicate, and magnesium silicate, and mixtures thereof. Particularly preferred are mixtures of $SiO_2$ with $Al_2O_3$ and mixtures of $SiO_2$ with MgO. Preference is given to a stoneware composed of 60 to 80 wt %, preferably about 70 wt % of $SiO_2$ and 20 to 40 wt % of $Al_2O_3$. Such materials may further comprise $Fe_2O_3$ and $TiO_2$, preferably in amounts of 2 to 3 wt %, and also $K_2O$ and $Na_2O$, preferably in amounts of 2.5 to 3.5 wt %, and additionally MgO and CaO, preferably in amounts of 0.5 to 1 wt %. The overall amount makes 100 wt %. A corresponding stoneware has a density, for example, of 2 to 2.5 $g/cm^3$, preferably about 2.3 $g/cm^3$. An example of a suitable material is ACIDUR® specialty stoneware from Vereinigte Füllkörper-Fabriken, Ransbach-Baumbach.

Steatite is additionally preferred. Steatite of type C 220 is particularly preferred. Especially preferred is steatite of type C 220 from CeramTec.

The BET surface area of the shaped support body is less than 0.5 $m^2/g$, preferably less than 0.3 $m^2/g$, more particularly less than 0.1 $m^2/g$. The lower limit for the BET surface area is preferably 0.001 $m^2/g$, more preferably 0.01 $m^2/g$. The shaped support body ought to have a high mechanical stability, hence not generating any abraded material when it is used as an oxidation catalyst.

The shaped support body may have a pronounced surface roughness, since an increased surface roughness generally dictates an increased strength of adhesion of the active composition and/or precursor composition eggshell applied to the surface of the shaped support body. As described in WO2009/133 065 A, the surface roughness may be increased by application of a thin porous inorganic shell which is sintered together with the shaped support body.

The active composition content Q (in wt %) of the catalyst is the mass of the active composition, based on the sum of the masses of active composition and shaped support body. In practical terms, the active composition content Q may be determined as follows: To determine the mass of the active composition, the known mass of the shaped support body can be subtracted from the mass of a catalyst as determined experimentally, following the heat treatment to remove the binder. Furthermore, the mass of the active composition in a quantity of n coated shaped catalyst bodies may be determined by determining the active catalyst mass and subtracting the weight of the shaped support body, which is ascertained by multiplying the average shaped support body weight by the number of shaped support bodies. To increase the accuracy of measurement, it is possible to determine the mass of a multiplicity of catalysts or shaped support bodies and average the result. Determining the active composition content Q is possible, furthermore, by removing the active composition from the shaped support body by washing. For this purpose, for example, the coated catalyst may be boiled repeatedly with $NH_4OH$ and the resulting liquid may be decanted off. The support which remains may subsequently be dried. The active composition content is given by the difference between catalyst mass (determined before removal of the active composition by washing) and support mass (determined following removal of the active composition by washing), based on the catalyst mass.

The support material content of the catalyst is accordingly (100−Q) (in wt %).

Based on the overall mass of the catalyst, the active composition content is preferably 2 to 50 wt %, more preferably 5 to 40 wt %, more particularly 10 to 30 wt %.

The shaped support body used in accordance with the invention has the shape of a saddle whose saddle surface is curved oppositely in the two principal directions.

In geometry, a saddle surface is a surface which is curved oppositely, i.e., anticlastically, in the two principal directions. Normally these two principal directions are perpendicular to one another, and so include a 90° angle. In accordance with the invention, deviations of up to +/−20°, preferably +/−10°, more particularly +/−5° are possible. With particular preference the two principal directions are perpendicular to one another.

In the two principal directions, the saddle preferably covers an angle of 180°+/−20°, preferably 180°+/−10°, more particularly 180°+/−5°. The angle covered in each case is more preferably of 180°. For the corresponding angles, reference may be made to the description in EP-B-0 192 314 on page 4, lines 9 to 35.

If these two principal directions are designated as the x-direction and the y-direction, and the height of a point on the saddle surface is designated as F, then the functional value of F in the x-direction becomes smaller on departure from the saddle point, whereas departure from the saddle point in the y-direction is accompanied by an increase in the function F.

Figure 2:
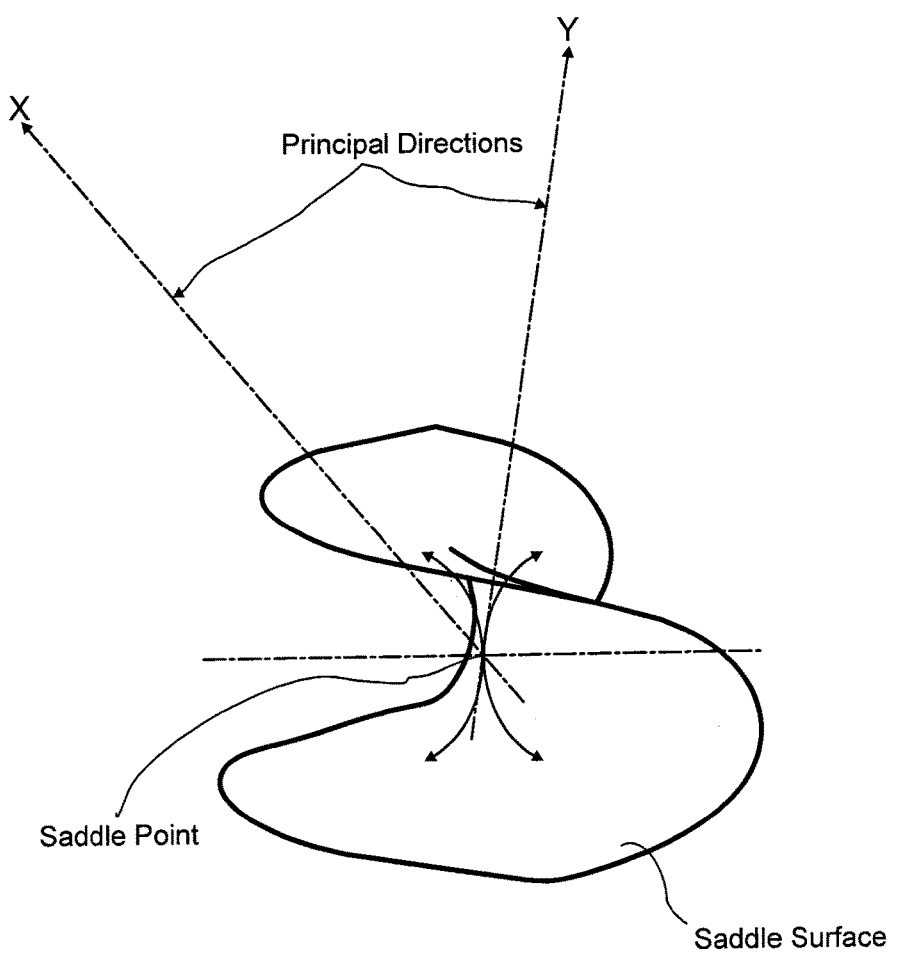
FIG. 2 shows a Berl saddle with ribs which run through the saddle point.

Saddle surface, saddle point, and principal directions are represented schematically in FIG. 2.

This description of a saddle point is the origin of the given name: a riding saddle is inclined downward perpendicular to the spinal column of the horse, and hence represents the x-direction, while in the y-direction—that is, parallel to the spinal column—it is upwardly shaped.

The for a description of saddle body shapes suitable in accordance with the invention, reference may be made to AT 333 704, EP-B-0 192 314, DE 522 572, and EP-B-0 218 766.

For example, the shaped support body may be designed as Intalox or Berl saddles. A Berl saddle is represented, for example, in DE 522 572 in the figures, and also in EP-B-0 218 766 in FIGS. 4 to 6. An Intalox saddle is shown, for example, in EP-B-0 218 766 in FIGS. 1 to 3, and also in EP-B-0 192 314 in the figures.

This shaped support body in the form of a saddle may have one or more ribs on the saddle surface, and these ribs may run, for example, through the saddle point or through the saddle points. A suitable arrangement of ribs is shown, for example, in EP-B-0 192 314 in FIGS. 4 and 5, and also in DE 522 572 in FIG. 3.

Figure 3:
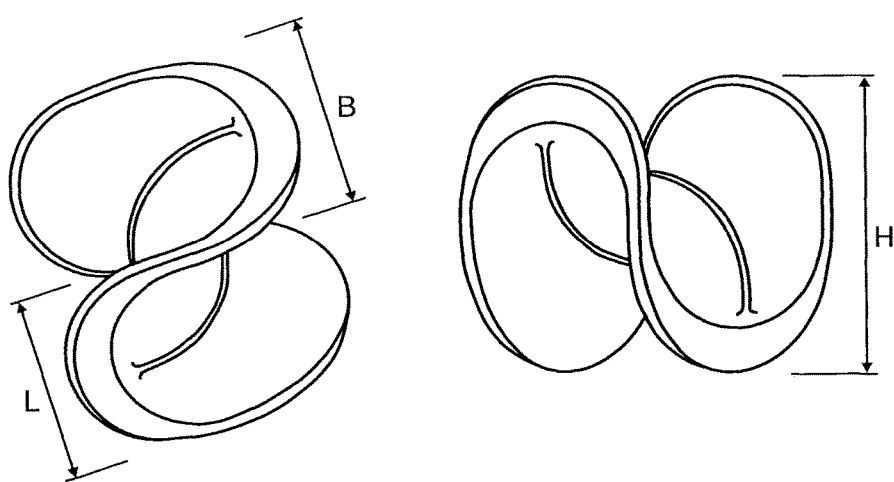
FIG. 3 shows an alternative Berl saddle which has projecting edges and a thickness profile which varies over its length.
Figure 4:
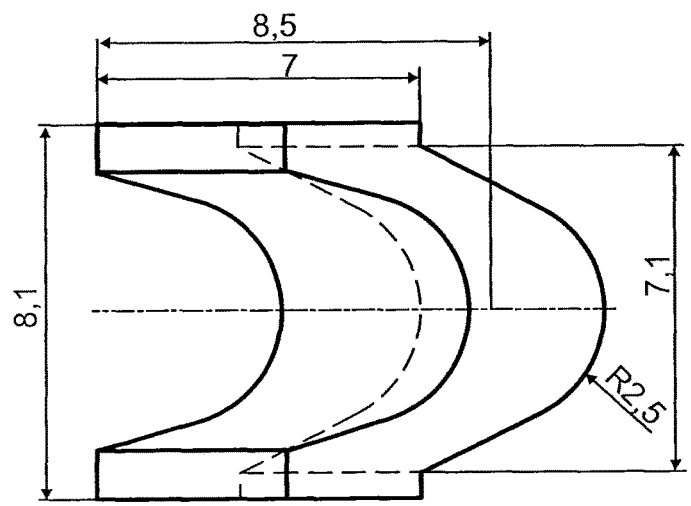
FIG. 4 shows an alternative Berl saddle which has projecting edges and a thickness profile which varies over its length.
Figure 4:
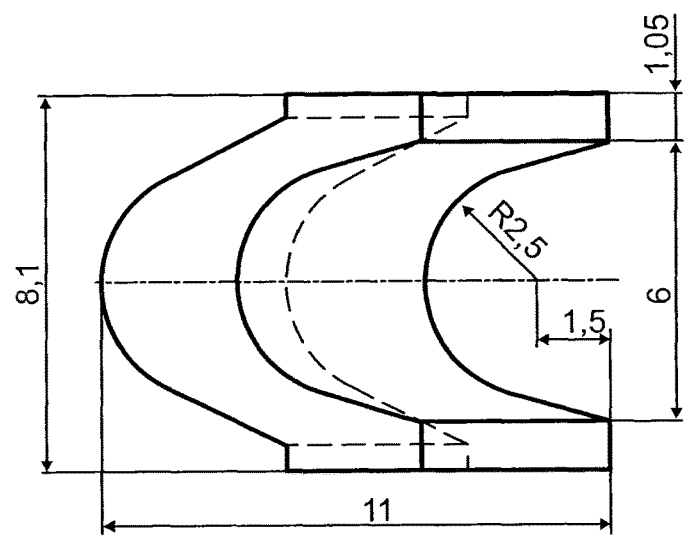
Figure 4:
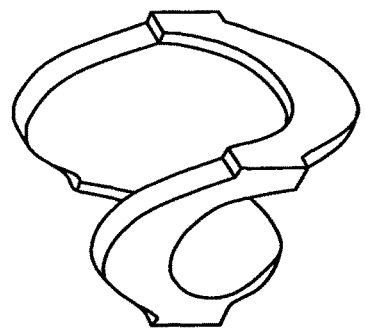

Saddles suitable in accordance with the invention are also represented schematically in FIGS. 1 and 4 of the appended drawing. FIG. 3 shows a Berl saddle with ribs which run through the saddle points and have a length L, breadth B, and height H. The maximum extent of the shaped support body is preferably 20 mm, more preferably 15 mm, more particularly 13 mm.

The length L and breadth B are each preferably in the range from 4 to 10 mm, the length L preferably corresponding to the breadth B. The height H is preferably in the range from 5 to 13 mm.

FIG. 2 shows a Berl saddle.

FIGS. 1 and 4 show an alternative Berl saddle which has projecting edges and a thickness profile which varies over its length. Such projecting edges and varying thickness profiles may come about within manufacturing tolerances, and are acceptable in relation to the function of the shaped support body. Projecting edges are formed, for example, when the shaped support body is produced by the tableting of a plastic starting composition.

The thickness of the saddles is preferably 0.1-0.5 times the radius, as represented in EP-B-0 192 314 on page 4, lines 39 to 40. The edges or angles of the saddle may be rounded off, as is the case with the Berl saddles, for example. Rounding of the angles or edges is preferred, since the angles are particularly sensitive to abrasion.

A further possibility is to provide the saddles with runoff channels or with holes or with both facilities at the same time. Through the gentle compression of the ends or through attachment of suitable conelets or ribs, the saddles can be prevented from intermeshing with one another. In order to obtain low stacking tendency, the saddle curve ought to be as steep as possible, or the aforementioned angle of about 180° ought to be maintained. A high wall thickness is also advantageous for low stacking tendency.

The multielement oxide used on the oxidation catalyst of the invention may be a known multielement oxide that catalyzes oxidation reactions. The multielement oxide and the catalyst as a whole are preferably free from metals with oxidation state 0—in other words, there are no metals in metallic form in the catalyst.

The multielement oxide and the oxidation catalyst as a whole are preferably free from precious metals. Precious metals in this context are the elements gold, silver, mercury, rhenium, ruthenium, rhodium, palladium, osmium, iridium, and platinum. In this regard, reference may be made to the "Edelmetalle" [Precious metals] entry heading in Römpp Chemielexikon, 9th edition.

Oxidation catalysts preferred in accordance with the invention are those for the catalytic gas phase oxidation of propene to acrolein, of propene or acrolein to acrylic acid, of tert-butanol, isobutene, isobutene, or tert-butyl methyl ether to methacrolein, of methacrolein or isobutyl aldehyde to methacrylic acid, of o-xylene and/or naphthalene to phthalic anhydride, or of alkene to alkadienes.

Suitable catalysts for the preparation of acrylic acid are described in, for example, EP-A-0 714 700 in claims 1, 21, and 23, and in DE-A-199 48 248, more particularly on pages 5, line 5 to page 7, line 15, and also page 9, line 37 to page 11, line 60.

Suitable catalysts for methacrylic acid preparation are described in, for example, EP-A-0 297 445, more particularly on page 5.

Suitable catalysts for the preparation of phthalic anhydride are described in, for example, WO 2012/014154, more particularly on page 3, line 20 to page 4, line 16.

Preferred active compositions are elucidated in more detail below.

Active compositions for preparation of an α,β-unsaturated carboxylic acid by gas phase oxidation of an α,β-unsaturated aldehyde are known per se. For example, catalytically active multielement oxide compositions comprising the elements Mo and V are suitable, where the molar proportion of the element Mo in the total amount of all elements other than oxygen in the catalytically active multielement oxide composition is 20 mol % to 80 mol %, the molar ratio of Mo present in the catalytically active multielement oxide composition to V present in the catalytically active multielement oxide composition, Mo/V, is 15:1 to 1:1. Preferably, the multimetal oxide also comprises at least one of the elements Nb and W; the corresponding molar ratio Mo/(total amount of W and Nb) is preferably 80:1 to 1:4.

Frequently, such multielement oxide compositions also comprise Cu in a corresponding molar ratio of Mo/Cu of 30:1 to 1:3.

The aforementioned multielement oxide compositions may, as well as the elements Mo, V, and optionally Nb and/or W or Cu, additionally comprise, for example, the elements Ta, Cr, Ce, Ni, Co, Fe, Mn, Zn, Sb, Bi, alkali metal (Li, Na, K, Rb, Cs), H, alkaline earth metal (Mg, Ca, Sr, Ba), Si, Al, Ti and Zr. Of course, the multielement oxide active composition may also consist solely of the elements Mo, V, O, and also Cu and optionally W and/or Nb. They are especially suitable as active compositions for catalysts for heterogeneously catalyzed partial gas phase oxidation of acrolein to acrylic acid.

Compositions of very particular suitability as active compositions for catalysts for heterogeneously catalyzed partial gas phase oxidation of acrolein to acrylic acid comprise catalytically active multielement oxide compositions conforming to the following general formula (I)

$$Mo_{12}V_aX^1_bX^2_cX^3_dX^4_eX^5_fO_n \quad (I)$$

in which
$X^1$ is W, Nb, Ta, Cr and/or Ce,
$X^2$ is Cu, Ni, Co, Fe, Mn and/or Zn,
$X^3$ is Sb and/or Bi,
$X^4$ is one or more alkali metals and/or alkaline earth metals and/or N,
$X^5$ is Si, Al, Ti and/or Zr,
a is a number in the range from 1 to 6,
b is a number in the range from 0.2 to 4,
c is a number in the range from 0 to 18, preferably from 0.5 to 18,
d is a number in the range from 0 to 40,
e is a number in the range from 0 to 4,
f is a number in the range from 0 to 40, and
n is the stoichiometric coefficient of the element oxygen, which is determined by the stoichiometric coefficients of the elements other than oxygen and their charge number in (I).

Preferably, the variables should be selected within the ranges specified with the proviso that the molar proportion of the element Mo in the total amount of all elements other than oxygen in the multielement oxide composition (I) is 20 mol % to 80 mol %, the molar ratio of Mo present in the catalytically active multielement oxide composition (I) to V present in the catalytically active multielement oxide composition (I), Mo/V, is 15:1 to 1:1, and the corresponding molar ratio Mo/(total amount of W and Nb) is 80:1 to 1:4 (and the corresponding molar ratio Mo/Cu is 30:1 to 1:3, if the multielement oxide composition comprises Cu).

The active composition preferably corresponds to the general formula (II)

$$Mo_{12}V_aW_bCu_cX^4_eX^5_fO_n \quad (II)$$

in which
$X^4$ is one or more alkali metals and/or alkaline earth metals,
$X^5$ is one or more elements from the group of Si, Al, Ti and Zr,
a is a number in the range from 2 to 4, advantageously a number in the range from 2.5 to 3.5,
b is a number in the range from 0 to 3, advantageously a number in the range from 0.2 to 3, preferably a number in the range from 0.5 to 2, more preferably a number in the range from 0.75 to 1.5, c is a number in the range from 0.5 to 3, advantageously a number in the range from 0.7 to 2.7, preferably a number in the range from 0.9 to 2.4, more preferably a number in the range from 1 to 1.5, e is a number in the range from 0 to 4, advantageously a number in the range from 0 to 2, preferably a number in the range from 0 to 1, more preferably a number in the range from 0 to 0.2, f is a number in the range from 0 to 40, advantageously a number in the range from 0 to 15, preferably a number in the range from 0 to 8, more preferably 0, and n is the stoichiometric coefficient of the element oxygen, which is determined by the stoichiometric coefficients of the elements other than oxygen and their charge number in (II).

Elements $X^4$ and $X^5$ are not necessarily part of the active composition of the general formula (II). They act generally as inert diluents within the active composition. The incorporation thereof into the active composition can be used to adjust the volume-specific catalyst activity to a desired level.

In general, the multielement coating is porous. It preferably has a particular distribution of pores of different mean diameters. The proportion by volume $p_{vol}$ of macropores is preferably at least 0.35, where $p_{vol}$ is determined by

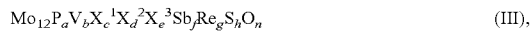

$$p_{vol} = \frac{V_{0.26-2}}{V_{0.02-6.5}}$$

in which $V_{0.26-2}$ is the volume of the pores having mean diameters in the range from 0.26 to 2 µm, and $V_{0.02-6.5}$ is the volume of the pores having mean diameters in the range from 0.02 to 6.5 µm.

The volume of the pores having mean diameters in the nanometer and micrometer range can be determined by mercury porosimetry (for example to DIN No. 66133). Mercury behaves as a non-wetting liquid with respect to most solids. Therefore, mercury is not spontaneously absorbed by the porous material but penetrates into the pores of the solid sample only under an external pressure. The level of this pressure depends on the size of the pores. This behavior is exploited in mercury porosimetry in order to find the pore diameter via the intrusion in volumetric terms at an externally applied pressure.

For the gas phase oxidation of methacrolein to methacrylic acid, the active composition preferably has a stoichiometry of the general formula III, $$Mo_{12}P_aV_bX^1_cX^2_dX^3_eSb_fRe_gS_hO_n \quad (III),$$

in which the definition of the variables is as follows:

$X^1$=potassium, rubidium and/or cesium, $X^2$=copper and/or silver, $X^3$=cerium, boron, zirconium, manganese and/or bismuth, a=0.5 to 3, b=0.01 to 3, c=0.2 to 3, d=0.01 to 2, e=0 to 2, f=0.01 to 2, g=0 to 1, h=0.001 to 0.5, and n=a number which is determined by the valency and frequency of the elements other than oxygen in III.

Preferred active compositions III are those in which h is 0.03 to 0.5.

Particularly preferred stoichiometry of the general formula III is that of working examples B1 to B15 from EP-A 467 144, even when these exemplary active compositions contain no K and/or no Re.

Aforementioned EP-A 467 144 also describes the use as catalysts for the heterogeneously catalyzed gas phase partial oxidation of methacrolein to methacrylic acid. These descriptions are also accurate in the context which exists in the present specification.

Active compositions of the general stoichiometry III may be prepared by finely dividing, as starting compounds, suitable salts of their constituent elemental ingredients, optionally at elevated temperature and with addition of acids or bases, in an aqueous medium by dissolution and/or suspension, mixing them optionally under inert gas in order to prevent unwanted oxidation processes, drying the mixture (e.g. by evaporation or spray drying), and applying the resulting dry composition, which has a finely divided form or has been converted into a finely divided form, to the shaped support body.

A preferred drying method for the aqueous solution or suspension of the sources of the elemental constituents of the desired active composition is spray drying.

In the context of the described mode of preparation of the active compositions of the general formula III, molybdenum is employed preferably in the form of an ammonium salt of molybdenic or phosphomolybdenic acid, vanadium generally as an ammonium vanadate or vanadium oxalate, phosphorus advantageously as orthophosphoric acid or diammonium phosphate, sulfur, for example, as ammonium sulfate, antimony customarily as antimony trioxide, rhenium, for example, as rhenium(VII) oxide, and the cationic metals normally as nitrates, oxides, hydroxides, carbonates, chlorides, formates, oxalates and/or acetates, and/or the hydrates of these.

For the preparation of phthalic anhydride, the multielement oxide composition preferably comprises 1 to 40 wt % of vanadium oxide, calculated as $V_2O_5$, 60 to 99 wt % of titanium dioxide, calculated as $TiO_2$, 0 to 1 wt % of a cesium compound, calculated as Cs, 0 to 1 wt % of a phosphorus compound, calculated as P, 0 to 10 wt % of antimony oxide, calculated as $Sb_2O_3$, whose total amount makes 100 wt %; for suitable sources of vanadium oxide and titanium dioxide, reference may be made to WO 2012/014154, page 3, line 29, to page 4, line 2. The titanium dioxide used ought to be in anatase structure. Suitable promoters contemplated include alkali metals, especially lithium, potassium and rubidium, in addition to the described cesium. They are employed typically in the form of their oxides or hydroxides. Furthermore, talium(I) oxide, aluminum oxide, zirconium oxide, iron oxide, nickel oxide, cobalt oxide, manganese oxide, tin oxide, silver oxide (less preferably), copper oxide, chromium oxide, molybdenum oxide, tungsten oxide, iridium oxide (less preferably), tantalum oxide, niobium oxide, arsenic oxide, antimony tetraoxide, antimony pentoxide, and cerium oxide may be used; see WO 2012/014154, page 4, lines 4 to 12.

For the oxydehydrogenation of alkenes to alkadienes, preferably of butene to butadiene, the active composition preferably has the general formula (IV)

$$Mo_{12}Bi_aFe_bCo_cNi_dCr_eX^1_fX^2_gO_x \quad (IV),$$

in which the variables are each defined as follows:

$X^1$=W, Sn, Mn, La, Ce, Ge, Ti, Zr, Hf, Nb, P, Si, Sb, Al, Cd and/or Mg;

$X^2$=Li, Na, K, Cs and/or Rb, a=0.1 to 7, preferably 0.3 to 1.5;

b=0 to 5, preferably 2 to 4;
c=0 to 10, preferably 3 to 10;
d=0 to 10;
e=0 to 5, preferably 0.1 to 2;
f=0 to 24, preferably 0.1 to 2;
g=0 to 2, preferably 0.01 to 1; and
x=a number which is determined by the valency and frequency of the elements in (IV) other than oxygen.

Catalysts suitable for the oxydehydrogenation are based generally on an Mo—Bi—O-containing multimetal oxide system which in general additionally comprises iron. The active compositions used for the oxydehydrogenation are also suitable for the oxidation of alkenes to α,β-unsaturated aldehydes, as set out in DE-A 102011079035, for example, though in that case usually in the absence of chromium. Generally speaking, the catalyst system also comprises further additional components from groups 1 to 15 of the Periodic Table, such as potassium, cesium, magnesium, zirconium, chromium, nickel, cobalt, cadmium, tin, lead, germanium, lanthanum, manganese, tungsten phosphorus, cerium, aluminum, or silicon, for example. Iron-containing ferrites as well have been proposed as catalysts.

In one preferred embodiment the multimetal oxide comprises cobalt and/or nickel. In another preferred embodiment the multimetal oxide comprises chromium. In another preferred embodiment the multimetal oxide comprises manganese.

Examples of Mo—Bi—Fe—O-containing multimetal oxides are Mo—Bi—Fe—Cr—O— or Mo—Bi—Fe—Zr—O-containing multimetal oxides. Preferred systems are described in, for example, U.S. Pat. No. 4,547,615 ($Mo_{12}BiFe_{0.1}Ni_8ZrCr_3K_{0.2}O_x$ and $Mo_{12}BiFe_{0.1}Ni_8AlCr_3K_{0.2}O_x$), U.S. Pat. No. 4,424,141 ($Mo_{12}BiFe_3CO_{4.5}Ni_{2.5}P_{0.5}K_{0.1}O_x+SiO_2$), DE-A 25 30 959 ($Mo_{12}BiFe_3Co_{4.5}Ni_{2.5}Cr_{0.5}K_{0.1}O_x$, $Mo_{13.75}BiFe_3Co_{4.5}Ni_{2.5}Ge_{0.5}K_{0.8}O_x$, $Mo_{12}BiFe_3Co_{4.5}Ni_{2.5}Mn_{0.5}K_{0.1}O_x$ and $Mo_{12}BiFe_3Co_{4.5}Ni_{2.5}La_{0.5}K_{0.1}O_x$), U.S. Pat. No. 3,911,039 ($Mo_{12}BiFe_3Co_{4.5}Ni_{2.5}Sn_{0.5}K_{0.1}O_x$), DE-A 25 30 959, and DE-A 24 47 825 ($Mo_{12}BiFe_3Co_{4.5}Ni_{2.5}W_{0.5}K_{0.1}O_x$).

Suitable multimetal oxides and their preparation are additionally described in U.S. Pat. No. 4,423,281 ($Mo_{12}Bi_bNi_8Pb_{0.5}Cr_3K_{0.2}O_x$ and $Mo_{12}Bi_bNi_7Al_3Cr_{0.5}K_{0.5}O_x$), U.S. Pat. No. 4,336,409 ($Mo_{12}BiNi_6Cd_2Cr_3P_{0.5}O_x$), DE-A 26 00 128 ($Mo_{12}BiNi_{0.5}Cr_3P_{0.5}Mg_{7.5}K_{0.1}O_x+SiO_2$), and DE-A 24 40 329 ($Mo_{12}BiCo_{4.5}Ni_{2.5}Cr_3P_{0.5}K_{0.1}O_x$).

Particularly preferred catalytically active multimetal oxides comprising molybdenum and at least one further metal have the general formula (IVa):

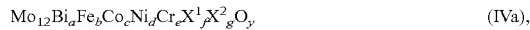

$$Mo_{12}Bi_aFe_bCo_cNi_dCr_eX^1_fX^2_gO_y \qquad (IVa),$$

where
$X^1$=Si, Mn and/or Al,
$X^2$=Li, Na, K, Cs and/or Rb,
$0.2 \leq a \leq 1$,
$0.5 \leq b \leq 10$,
$0 \leq c \leq 10$,
$0 \leq d \leq 10$,
$2 \leq c+d \leq 10$
$0 \leq e \leq 2$,
$0 \leq f \leq 10$
$0 \leq g \leq 0.5$
y=a number which is determined, subject to the proviso of charge neutrality, by the valency and frequency of the elements other than oxygen in (Ia).

Preferred catalysts are those whose catalytically active oxide composition has only Co of the two metals Co and Ni (d=0). With preference $X^1$ is Si and/or Mn, and $X^2$ is preferably K, Na and/or Cs, more preferably $X^2$=K.

The stoichiometric coefficient a in formula (IVa) is preferably $0.4 \leq a \leq 1$, more preferably $0.4 \leq a \leq 0.95$. The value for the variable b lies preferably in the range $1 \leq b \leq 5$ and more preferably in the range $2 \leq b \leq 4$. The sum of the stoichiometric coefficients c+d lies preferably in the range $4 \leq c+d \leq 8$, and more preferably in the range $6 \leq c+d \leq 8$. The stoichiometric coefficient e lies preferably in the range $0.1 \leq e \leq 2$, and more preferably in the range $0.2 \leq e \leq 1$. The stoichiometric coefficient g is judiciously $\geq 0$. Preferably $0.01 \leq g \leq 0.5$ and more preferably $0.05 \leq g \leq 0.2$.

The value of the stoichiometric coefficient of oxygen, y, is dictated by the valency and frequency of the cations, subject to the proviso of charge neutrality. Favorable eggshell catalysts of the invention are those having catalytically active oxide compositions whose molar ratio Co/Ni is at least 2:1, preferably at least 3:1 and more preferably at least 4:1. Ideally there is only Co present.

Suitable finely divided multimetal oxide compositions are produced starting from known starting compounds of the nonoxygen elemental constituents of the desired multimetal oxide composition in the respective stoichiometric proportion, and these compounds are used to generate an extremely intimate, preferably finely divided dry mixture, which is then subjected to a heat treatment (calcination). The sources here may either already be oxides, or may be compounds which can be converted into oxides by heating, at least in the presence of oxygen. Besides the oxides, therefore, starting compounds contemplated include in particular halides, nitrates, formates, oxalates, acetates, carbonates, or hydroxides.

Suitable starting compounds of molybdenum are also its oxo compounds (molybdates) or the acids derived from them. Ammonium heptamolybdate is a preferred starting compound of molybdenum.

Suitable starting compounds of Bi, Cr, Fe and Co are their nitrates in particular.

The intimate mixing of the starting compounds may take place in principle in a dry form or in the form of the aqueous solutions or suspensions.

An aqueous suspension, for example, may be prepared by combining a solution which comprises at least molybdenum with an aqueous solution which comprises the remaining metals. Alkali metals or alkaline earth metals may be present in both solutions. The combining of the solutions results in a precipitation, leading to the formation of a suspension. The precipitation temperature may be higher than room temperature, preferably from 30° C. to 95° C., and more preferably from 35° C. to 80° C. The suspension thereafter may be aged at elevated temperature for a certain time. The aging time is generally between 0 and 24 hours, preferably between 0 and 12 hours, and more preferably between 0 and 8 hours. The aging temperature is generally between 20° C. and 99° C., preferably between 30° C. and 90° C., and more preferably between 35° C. and 80° C. While the suspension is being precipitated and aged, it is generally mixed by stirring. The pH of the mixed solutions or suspension is generally between pH 0 and pH 12, preferably between pH 0.5 and pH 4, and more preferably between pH 1 and pH 3.

Removal of the water produces a solid which represents an intimate mixture of the added metal components. The drying step may be carried out in general by evaporation, spray drying or freeze drying or the like. Drying takes place preferably by spray drying. The suspension for this purpose is atomized at elevated temperature using a spraying head, this spraying head being at a temperature in general of 120° C. to 300° C., and the dried product is collected at a temperature of >60° C. The residual moisture content, as determined by drying of the spray powder at 120° C., is generally less than 20% by weight, preferably less than 15% by weight and more preferably less than 12% by weight.

An inventive catalyst is generally obtained by applying a pulverulent active composition to a shaped support body, preferably by the preparation processes described hereinafter.

The pulverulent active composition can be prepared in different ways. In one embodiment, the active composition is prepared by using sources of the elemental constituents of the active composition to produce an intimate dry mixture which is calcined at temperatures of 350 to 600° C. and then converted to powder form.

Preferred sources of the elemental constituents of the active composition are oxides of metals present in the active composition. Useful sources of the elemental constituents of the active composition also include compounds which can be converted to oxides by heating, at least in the presence of oxygen; especially halides, nitrates, formates, oxalates, citrates, acetates, carbonates, amine complexes, ammonium salts and/or hydroxides of metals present in the active composition.

Preferably, the intimate dry mixture is produced by intimately mixing the sources. The intimate mixing can be effected in dry or wet form. If it is effected in dry form, the sources are appropriately used in the form of finely divided powders. Particularly intimate dry mixtures are obtained in the course of mixing when the starting materials are exclusively sources present in dissolved form. Therefore, the intimate mixing of the sources is preferably effected in wet form. Preferably, the sources are mixed with one another in the form of solutions and/or suspensions and the resulting wet mixture is subsequently dried to give the intimate dry mixture. The solvents and/or suspension media used are preferably water or an aqueous solution. The wet mixture is preferably dried by spray drying with exit temperatures of 100 to 150° C. The drying gas stream is preferably air or molecular nitrogen.

Before the calcination, the dry mixture resulting from the drying procedure may also be subjected to an operation of mixing. Particularly advantageously, the mixing operation is performed after addition of a liquid, which may, for example, be water, acetic acid or the like, as a kneading operation. The shear forces which act comminute agglomerates and ultimately produce a well-homogenized pastelike material, which can then readily be processed into stable extrudates which can be dried. The dried extrudates are advantageously suitable, inter alia, for calication in a rotary tube. The calcination can be performed either under inert gas or under an oxidative atmosphere, or else under a reducing atmosphere. Preferably, the calcination is performed under an oxidative atmosphere. Useful inert gases are especially nitrogen, water vapor, noble gases, and mixtures thereof. The oxidative atmosphere preferably comprises oxygen, especially air. The reducing atmosphere comprises preferably $H_2$, $NH_3$, CO, methane and/or acrolein. The catalytic activity of the active composition as per (I) and (II) for the partial gas phase oxidation of acrolein to acrylic acid generally exhibits an optimum depending on the oxygen content of the calcination atmosphere. Preferably, the oxygen content of the calcination atmosphere is 0.5 to 10% by volume, more preferably 1 to 5% by volume. Oxygen contents above and below the aforementioned limits normally reduce the resulting catalytic activity. The calcination time may be a few minutes to a few hours and typically decreases with the level of the calcination temperature. A calcination process of good suitability is described, for example, by DE-A 103 60 057.

The calcining of the dry mixture gives the active composition. The conversion to powder form is preferably effected by grinding.

In an alternative process for preparing the catalyst, finely divided precursor composition is first applied to the surface of the shaped support body and the calcination of the precursor composition to the active composition is performed on the surface of the shaped support body. The finely divided precursor composition preferably comprises sources of the elemental constituents of the active composition. The active composition is preferably an active composition of the general formula (I) or (II) or (III) or (IV).

In a process according to the invention for preparing the catalyst, the shaped support body is coated with the active composition by mixing a multitude of shaped support bodies, a pulverulent active composition and a liquid binder, without saturating the pulverulent active composition with the liquid binder, in a vessel, the duration of the coating operation being less than 60 minutes. The saturation of the pulverulent active composition with the liquid binder is avoided by selecting the ratio of the amount of liquid binder to the amount of pulverulent active composition such that the amount of binder remains below the liquid absorption capacity of the pulverulent active composition.

The liquid absorption capacity of powders can be determined, for example, by stirring up the powder in a stirrer and applying liquid to the stirred powder and measuring the torque at the stirrer motor against time. The amount of liquid which has been applied to the powder up to the maximum torque can be used to calculate the liquid absorption capacity of the powder.

The pulverulent active composition preferably has a numerical fraction of particles having a longest dimension above 50 µm of less than 1%.

The term "binder" is understood to mean substances which permanently or temporarily improve the adhesion of the active composition powder particles to one another and/or to the support material. Preferably, the binder essentially evaporates or sublimes in the course of subsequent drying. In the process according to the invention, the binders used may, for example, be polyols such as ethylene glycol, propylene glycol, butylene glycols, glycerol, or amides such as formamide, N,N-dimethylformamide, N,N-diethylformamide, N,N-dibutylformamide, acetamide, pyrrolidone or N-methylpyrrolidone. The liquid binder is preferably selected from water, glycerol and solutions of glycerol in water. A preferred liquid binder is a solution of glycerol in water comprising 20 to 99% by weight of water. A particularly preferred liquid binder is a solution of glycerol in water comprising 75% by weight of water.

Preferably, the shaped support bodies are placed in the vessel at the start, and the pulverulent active composition and the liquid binder are added separately to the vessel over the duration of coating. Thus, the pulverulent active composition and the liquid binder are contacted with one another only in the vessel. The pulverulent active composition and the liquid binder are preferably combined only on the surface of the shaped support bodies initially charged in the vessel. This is achieved by spraying the liquid binder into the vessel and introducing the pulverulent active composition into a region of the vessel outside the spray cone of the liquid binder. In this way, local overloading of the powder particles with liquid is avoided. The pulverulent active composition and the liquid binder can be introduced into the vessel over the duration of the treatment, for example, by continuous addition or by separate addition of portions over time.

The mixing is preferably effected by continuous movement of the vessel. The movement is preferably a rotational movement.

The process principle disclosed in DE-A 2909671 (cf. also EP-A 714 700 and DE-A 10 2005 010 645) using the liquid binder desired in each case is particularly suitable for performance of the above-described process for preparing the catalyst.

In other words, the shaped support bodies to be coated are introduced into a preferably inclined (the angle of inclination is generally 30 to 90°) rotating vessel (for example rotary pan or coating tank or coating drum). Suitable rotary vessels for this end use are especially the Hi-Coater HCF-100 from Freund Industrial Co., Ltd, Tokyo (JP), and the Hi-Coater LH 100 from Gebrüder Lödige Maschinenbau GmbH, Paderborn, Germany.

The rotating vessel conducts the shaped support bodies under two metering apparatuses arranged in succession at an advantageous separation. The first of the two metering devices appropriately corresponds to a nozzle, by which the shaped support bodies rolling within the rotating pan (Hi-Coater) are moistened in a controlled manner with the liquid binder. Appropriately in application terms, the second metering apparatus is outside the atomization cone of the liquid binder sprayed in, and serves to supply the pulverulent active composition (for example via a shaking channel). The shaped support bodies take up the active composition, the active composition is compacted to a coherent shell on the external surface of the shaped support bodies through the rolling motion. The thus base-coated shaped support body, in the course of the subsequent rotation, again passes through the spray nozzle, is moistened in a controlled manner (optionally with another liquid binder), in order to be able to take up a further layer of (optionally another) pulverulent active composition in the course of further movement etc. (intermediate drying is generally not required). The at least partial removal of the liquid binder used can, for example, following the teaching of EP-A 714 700 or the teaching of DE-A 10 2005 010 645, be effected by final supply of heat, for example through the action of hot gases such as N2 or air (these are fed in and removed through spatially separated wall elements configured like a grid in the rotary pan, or coating tank, or coating drum (rotary vessel in general)).

The support surface is appropriately moistened in such a way that it has adsorbed liquid binder but this is not visually apparent on the support surface. If the shaped support body surface is too moist, there is twinning, i.e. agglomeration of the shaped support bodies per se rather than the active composition and/or precursor composition adhering to the surface of the shaped support body. More detailed information in this regard can be found in DE-A 2909671, in EP-A 714 700 and in DE-A 10 2005 010 645. One benefit of the procedure described is that the removal of the liquid binder used can be undertaken in a comparatively controlled manner, for example through evaporation and/or sublimation. In the simplest case, this can be effected, as already explained, through the action of hot gases at appropriate temperature (frequently 50 to 150° C.). Such an action of hot gases generally brings about preliminary drying.

Application of the active composition to the shaped support bodies may also be accomplished by coating with a suspension in a fluidized bed, as described in WO 2005/030388, DE 4006935 A1, DE 19824532 A1, EP 0966324 B1, for example. The support is fluidized in, for example, a fluidized bed or fluid-bed apparatus in an ascending stream of gas, more particularly air. The apparatus consists usually of a conical or spherical container in which the fluidizing gas is introduced from below or from above via an immersed tube. The suspension is sprayed into the fluidized bed via nozzles from above, from the side or from below. The use of an ascending tube disposed centrally and/or concentrically around the immersed tube is advantageous. The gas velocity prevailing within the ascending tube is relatively high, and transports the support particles upward. Within the outer ring, the gas velocity is only a little above the fluidization velocity. Accordingly, the particles are moved vertically in a circular manner. A suitable fluid-bed apparatus is described in DE-A 4006935, for example.

The removal of the binder can be effected within a drying apparatus of any kind (for example in a belt dryer) and/or or not until within the fixed catalyst bed of the shell and tube reactor, as recommended, for example, by DE-A 10 2005 010 645. Preferably, the inventive catalyst is obtained by removing the liquid binder from the coated shaped support body by drying at a temperature in the range from 150 to 400° C., preferably 250 to 350° C. The drying is preferably conducted in an air stream. Preferably, the duration of drying is 0.5 to 8 h, more preferably 1 to 4 h.

The invention also provides a process for preparing an $\alpha,\beta$-unsaturated carboxylic acid by gas phase oxidation of an $\alpha,\beta$-unsaturated aldehyde with molecular oxygen over a fixed catalyst bed, which comprises a bed of an inventive catalyst. Preferably, the molecular oxygen and the $\alpha,\beta$-unsaturated aldehyde are contacted with the fixed catalyst bed by conducting the molecular oxygen and the $\alpha,\beta$-unsaturated aldehyde over the fixed catalyst bed. Preferably, a reaction gas comprising the molecular oxygen and the $\alpha,\beta$-unsaturated aldehyde is conducted over the fixed catalyst bed and the reaction gas is thus converted to a product gas.

The $\alpha,\beta$-unsaturated aldehyde is preferably selected from $\alpha,\beta$-unsaturated aldehydes comprising 3 to 6 (i.e. 3, 4, 5 or 6) carbon atoms, especially from acrolein and methacrolein. More preferably, the $\alpha,\beta$-unsaturated aldehyde is acrolein. The process is particularly suitable for preparation of $\alpha,\beta$-unsaturated carboxylic acids, especially for oxidation of acrolein to acrylic acid and of methacrolein to methacrylic acid. It is preferably a process for preparing acrylic acid by gas phase oxidation of acrolein.

The molecular oxygen is preferably supplied to the process in the form of air.

The proportion of the $\alpha,\beta$-unsaturated aldehyde present in the reaction gas will generally be 3 to 15% by volume, preferably 4 to 10% by volume, more preferably 5 to 8% by volume, based in each case on the reaction gas.

Preferably, the reaction gas also comprises at least one inert diluent gas other than water vapor. This is understood to mean those gases which, in the course of the gas phase oxidation, remain chemically unchanged to an extent of at least 95 mol %, preferably to an extent of at least 98 mol %. Examples of inert diluent gases are $N_2$, $CO_2$ and noble gases such as Ar. The inert diluent gas used is preferably molecular nitrogen. The inert diluent gas may comprise at least 20% by volume, preferably at least 40% by volume, further preferably at least 60% by volume, more preferably at least 80% by volume, most preferably at least 95% by volume, of molecular nitrogen.

The reaction gas may also comprise water vapor.

The reaction gas may also comprise cycle gas. Cycle gas is understood to mean the residual gas which remains when α,β-unsaturated carboxylic acid and other less volatile constituents are essentially selectively separated from the product gas of the gas phase oxidation.

Preferably, the process according to the invention for preparing the α,β-unsaturated carboxylic acid forms the second stage of a two-stage gas phase oxidation of an alkene to the α,β-unsaturated carboxylic acid. In the course of such a two-stage gas phase oxidation, the product gas of the first stage is preferably supplied to the second stage. Before being supplied to the second stage, the product gas from the first stage can, for example, be cooled and/or oxygen can be added (secondary addition of oxygen, preference being given to the addition of air). The cycle gas is preferably conducted into the first of the two stages.

In the reaction gas, the molar ratio of $O_2$:α,β-unsaturated aldehyde is preferably 1 to 3, more preferably 1 to 2, very preferably 1 to 1.5.

The reaction gas preferably comprises α,β-unsaturated aldehyde:oxygen:water vapor:inert diluent gas other than water vapor in a volume ratio of 1:(1 to 3):(0 to 20):(3 to 30), preferably of 1:(1 to 3):(0.5 to 10):(7 to 10).

Preferably, the space velocity of α,β-unsaturated aldehyde on the bed is not more than 600 l (STP)/(lh), preferably not more than 300 l (STP)/(lh), more preferably not more than 250 l (STP)/(lh). The space velocity of α,β-unsaturated aldehyde on the bed expressed in l (STP)/(lh) is understood to mean the amount of α,β-unsaturated aldehyde in standard liters which is conducted over the fixed catalyst bed as a constituent of the reaction gas per hour per liter of bed. One standard liter (l (STP)) is the volume in liters that the molar amount of an ideal gas corresponding to the molar amount of α,β-unsaturated aldehyde would occupy under standard conditions, i.e. at 0° C. and 1 bar.

In general, a total pressure of 0.5 to 100 bar, preferably of 1 to 5 bar, especially of 1 to 3 bar, exists in the reaction gas. All pressure figures in this document relate to absolute pressures.

Preferably, the oxidation process, more particularly the process for preparing the α,β-unsaturated carboxylic acid is performed in a shell and tube reactor, the reaction tubes of which have been filled with the fixed catalyst bed.

The shell and tube reactor is preferably a two-zone shell and tube reactor. A preferred two-zone shell and tube reactor is disclosed by DE-C 28 30 765. But the two-zone shell and tube reactors disclosed in DE-C 25 13 405, U.S. Pat. No. 3,147,084, DE-A 22 01 528, EP-A 383224 and DE-A 29 03 582 are also suitable.

In the two-zone shell and tube reactor, two essentially spatially separate temperature control media are preferably conducted around the reaction tubes. The temperature control media are preferably salt melts. The entrance temperature of the temperature control medium is preferably set to 230 to 300° C., preferably to 240 to 290° C., more preferably to 250 to 285° C. The temperature control medium can be conducted in cocurrent or in countercurrent to the reaction gas mixture through the respective temperature control zone. Within the temperature control zone, the temperature control medium is preferably conducted in a meandering manner. The flow rate of the temperature control media within the respective temperature control zone is preferably selected such that the temperature of the heat exchange medium from the inlet site into the temperature zone to the outlet site from the temperature zone rises by 0 to 15° C., frequently 1 to 10° C., or 2 to 8° C., or 3 to 6° C.

In a preferred embodiment, the fixed catalyst bed comprises at least two successive reaction zones, in which case the bed, at least in the reaction zone in which the highest local temperature occurs, comprises an inventive catalyst.

The bed may, for example, consist exclusively of inventive catalysts. It is also possible for substantially homogeneous mixtures of inventive catalysts and shaped diluent bodies which are essentially inert with respect to the gas phase oxidation to be present in the bed. Useful materials for the shaped diluent bodies include, for example, porous or nonporous aluminum oxides, silicon dioxide, zirconium dioxide, silicon carbide, silicates such as magnesium silicate or aluminum silicate and/or steatite (for example of the C220 type from CeramTec, Germany).

The geometry of the shaped diluent bodies may in principle be as desired. In other words, they may, for example, be rings, spheres, tablets, punched tablets, trilobes, punched trilobes, star extrudates, star tablets, wagonwheels, extrudates, pills, cylinders and hollow cylinders.

In general, the shell and tube reactor additionally has thermal tubes to determine the gas temperature in the catalyst bed. Appropriately, the internal diameter of the thermal tubes and the diameter of the accommodating sleeve within for the thermocouple is selected such that the ratio of volume which evolves heat of reaction to heat-removing surface area is the same or only slightly different in thermal tubes and reaction tubes.

The pressure drop should be the same in reaction tubes and thermal tubes, based on the same GHSV. Any pressure drop in the thermal tube can be balanced out, for example, by adding spalled catalyst to the catalysts. This balancing is appropriately homogeneous over the entire thermal tube length. For the rest, the filling of thermal tubes may be configured as described in EP-A 873783.

The temperatures measured in the thermal tubes can be used to determine the highest local temperature of the fixed catalyst bed and the position thereof in the fixed catalyst bed.

The catalytic gas phase oxidation of methacrolein to methacrylic acid employing the shaped catalyst bodies obtainable as described may take place in a manner which is known per se, being described in EP-A 467 144, for example. The oxidizing agent, oxygen, may be used in the form, for example, of air, or alternatively in pure form. On account of the great heat of reaction, the reactants are preferably diluted with inert gases such as $N_2$, CO, $CO_2$ and/or with water vapor. Operation takes place preferably at a methacrolein:oxygen:water vapor:inert gas ratio of 1:(1 to 3):(2 to 20):(3 to 30), more preferably of 1:(1 to 3):(3 to 10):(7 to 18). The methacrolein fraction of the initial reaction gas mixture is generally 4% to 11%, frequently 4.5% to 9%, by volume. In order to prevent explosive mixtures, the oxygen content is restricted preferably to ≤12.5% by volume. This is achieved more preferably by recycling a substream of the off-gas removed from the reaction product. Moreover, the gas phase partial oxidation to methacrylic acid is accomplished typically at overall space velocities on the fixed catalyst bed of 600 to 1800 l (STP)/l·h, or at methacrolein velocities of 40 to 100 l (STP/l·h.

Phthalic anhydride may be prepared under reaction conditions as stated in WO 2012/014154.

The present invention also provides for the use of the eggshell catalysts of the invention in a process for the oxidative dehydrogenation of 1-butene and/or 2-butene to butadiene. The catalysts of the invention are notable for high activity, but also, in particular, for high selectivity with regard to the formation of 1,3-butadiene from 1-butene and 2-butene. For the implementation of the process, reference may be made to WO 2009/124974 and WO 2009/124945, for example.

The invention also provides a process for the oxidative dehydrogenation of n-butenes to butadiene, which involves mixing a starting gas mixture comprising n-butenes with an oxygen-comprising gas and optionally with additional inert gas or water vapor and contacting the mixture in a fixed bed reactor at a temperature of 220 to 490° C. with a catalyst of the invention arranged in a fixed catalyst bed.

The invention is illustrated by the examples hereinafter.

I. Preparation of Catalysts for the Oxidation of Acrolein

A) Preparation of a Precursor Composition

In a water-heated 1.75 m³ jacketed stainless steel vessel having a beam stirrer, 8.2 kg of copper acetate hydrate (content: 32.0% by weight of Cu, addition rate 50 kg/h, from Goldschmidt) were dissolved in 274 l of water at room temperature (~25° C.) while stirring (speed: 70 revolutions/min). A solution 1 was obtained. This was stirred for a further 30 min.

Spatially separately from this, a water-heated 1.75 m³ jacketed stainless steel vessel having a beam stirrer (speed: 70 revolutions/min) was initially charged with 614 l of water and heated to 40° C., and 73 kg of ammonium heptamolybdate tetrahydrate (81.5% by weight of MoO₃, addition rate 300 kg/h, from H.C. Starck GmbH) were stirred in while maintaining the 40° C. Then the vessel contents were heated to 90° C. within 30 min while stirring and, while maintaining this temperature, the following were stirred in successively and in the sequence mentioned: 12.1 kg of ammonium metavanadate (77.6% of V₂O₅, addition rate 150 kg/h, further stirring time after addition 40 min) and 10.7 kg of ammonium paratungstate heptahydrate (89.6% by weight of WO₃, addition rate 50 kg/h, further stirring time after addition 30 min). A solution 2 was obtained.

Solution 2 was cooled to 80° C. and then solution 1 was transferred into solution 2 rapidly at a stirrer speed of the beam stirrer of 70 revolutions/min, and stirred in. The mixture obtained was admixed with 133 l of a 25% by weight aqueous $NH_3$ solution at a temperature of 25° C. While stirring, a clear solution formed, which briefly had a temperature of 65° C. and a pH of 8.5. It was drained into a further water-heated 1.75 m³ jacketed stainless steel vessel having a beam stirrer. The vessel contents were heated to 80° C., stirred at a stirrer speed of 40 revolutions/min and circulated. The pH of the vessel contents was kept at a value of 8.5 by means of automatic addition of a 25% by weight aqueous $NH_3$ solution. The vessel contents were pumped into the rotary disk spray tower of the FS 15 type from Niro (Denmark) and dried in a hot air cocurrent at a gas inlet temperature of 350±10° C., a disk speed of 15 000 rpm and a combustion air volume flow rate of 2300 m³ (STP)/h, while maintaining a reduced pressure of 1 mbar in the spray tower. The liquid volume flow rate metered into the spray tower was regulated such that a gas outlet temperature of 110±5° C. was attained. The resulting spray powder had a particle diameter of 2 to 50 μm and an ignition loss of 21±2% by weight. The ignition loss was determined by heating in a porcelain crucible (3 h at 600° C.) under air. The porcelain crucible had been calcined at 900° C. to constant weight beforehand. The spray powder was dispensed into special containers or special vats (200 liters) with a plastic inlet. To remove all lumps, a sieve insert was used.

75 kg of spray powder thus obtained were metered into a kneader from AMK (Aachener Misch- and Knetmaschinen Fabrik) of the VM 160 type (sigma blades) at a screw speed of 15 revolutions/min. Subsequently, 6.5 l of acetic acid (100% by weight, glacial acetic acid) and 5.2 l of water were metered into the kneader at a screw speed of 15 revolutions/min. After a kneading time of 4 to 5 minutes (speed of the screw: 20 revolutions/min), a further 6.5 l of water were added and the kneading operation was continued until 30 minutes had passed (kneading temperature about 40 to 50° C.). In the course of kneading, the power consumption was observed. On exceedance of a power consumption of 25%, about another 1 l of water were added to the kneading material if required. Thereafter, the kneading material was emptied into an extruder and shaped by means of the extruder (from Bonnot Company (Ohio), type: G 103-10/D7A-572K (6" Extruder W Packer) to give extrudates (length: 1-10 cm; diameter 6 mm). In a 3-zone belt dryer, the extrudates were dried at a belt speed of 10 cm/min and a resulting residence time of 64 min and a gas inlet temperature of 155° C. The expected values for the gas temperatures are 90-95° C. in zone 1, about 115° C. in zone 2 and about 125° C. in zone 3.

B) Preparation of an Active Composition of the Formula $Mo_{12}V_3W_{1.2}Cu_{1.2}O_n$ The thermal treatment was performed in the rotary tube oven described in DE 10360057A1, under the following conditions:
the thermal treatment was effected batchwise with a material amount of 306 kg, which had been prepared as described under A);
the angle of inclination of the rotary tube to the horizontal was ≈0°;
the rotary tube rotated to the right at 1.5 revolutions/min;
over the course of the entire thermal treatment, a gas stream of 205 m³ (STP)/h was conducted through the rotary tube, which (after displacement of the air originally present) had the following composition and was supplemented at the outlet thereof from the rotary tube by a further 25 m³ (STP)/h of barrier gas nitrogen: 80 m³ (STP)/h composed of baseload nitrogen and gases released in the rotary tube, 25 m³ (STP)/h of barrier gas nitrogen, 30 m³ (STP)/h of air and 70 m³ (STP)/h of recirculated cycle gas. The barrier gas nitrogen was supplied at a temperature of 25° C. The mixture of the other gas streams, coming from the heater, was in each case conducted into the rotary tube at the temperature that each material had in the rotary tube.

Within 10 h, the material temperature was raised from 25° C. in an essentially linear manner to 300° C.; then the material temperature was raised in an essentially linear manner to 360° C. within 2 h; subsequently, the material temperature was lowered in an essentially linear manner to 350° C. within 7 h; then the material temperature was increased in an essentially linear manner to 420° C. within 2 h and this material temperature was maintained for 30 min; then the 30 m³ (STP)/h of air in the gas stream conducted through the rotary tube were replaced by a corresponding increase in the baseload nitrogen (which ended the operation of the actual thermal treatment), the heating of the rotary tube was switched off and the material was cooled to a temperature below 100° C. by switching on the rapid cooling of the rotary tube by inward suction of ambient air within 2 h, and finally to room temperature; the gas stream was fed to the rotary tube here at a temperature of 25° C.; over the entire thermal treatment, the pressure (immediately) beyond the rotary tube outlet of the gas stream was 0.2 mbar below the external pressure.

The oxygen content of the gas atmosphere in the rotary tube oven in all phases of the thermal treatment was 2.9% by volume. Over the total duration of the reductive thermal treatment, on arithmetic average, the ammonia concentration of the gas atmosphere in the rotary tube oven was 4% by volume.

The catalytically active material obtained was ground by means of a biplex crossflow classifying mill (BQ 500) (from Hosokawa-Alpine Augsburg) to give a finely divided powder P. 24 long blades were installed here into the milling tracks. The milling speed was 2500 revolutions/min. The ventilator throttle flap was fully open. The dosage was set to 2.5 revolutions/min. The air output volume flow rate was 1300 m$^3$/h, the pressure differential 10-20 mbar. 50% of the powder particles of the finely divided powder resulting from the grinding passed through a sieve of mesh size 1 to 10 μm. The proportion of particles having a longest dimension above 50 μm in the finely divided powder was less than 1%.

C) Shaping of the Active Composition

C1 (Comparative Example) Ring 7×3×4 with Internal Surface (Hollow Cylinder)

1600 g of hollow cylindrical support bodies (external diameter 7 mm, length 3 mm, internal diameter 4 mm, C220 steatite from CeramTec having a surface roughness $R_z$ of 45 μm (grit layer)) were coated with the ground finely divided powder P. The coating was effected in a HiCoater LHC 25/36 (from Lödige, D-33102 Paderborn). This HiCoater had been modified in order to enable continuous powder metering. This consisted of a funnel-shaped powder reservoir, which was connected via a Tygon hose (internal diameter: 8 mm, external diameter 11.1 mm; from Saint-Gobain Performance, 89120 Charny, France) to the drum of the HiCoater. The drum radius was 18 cm. The depth of the drum is 20 cm. The axis about which the drum rotated was aligned horizontally. For the coating, 600 g of the ground catalytically active oxide composition powder were introduced into the powder reservoir. The powder was metered in by continuous pressure metering. The pulse-timed valve was set to 50 ms and the pressure set was 0.7 bar above ambient pressure (~1 atm). The powder in the funnel-shaped powder reservoir was stirred continuously during the coating in order to ensure homogeneous metering (stirrer run time: 2 s, stirrer pause time: 1 s, modified V-shaped anchor stirrer, built in-house at BASF SE). The binder was an aqueous solution of 75% by weight of water and 25% by weight of glycerol. This was sprayed into the drum separately via a liquid metering device. The liquid was pumped with a Watson-Marlow HPLC pump (323 type) into the metering arm, which is within the drum (spray pressure 3 bar, forming pressure 2 bar, flow rate: 3 g of glycerol/water solution (1:3)/min). The powder metering and liquid metering devices are arranged parallel to one another. The nozzle from Schlick (DE) of the 570/0 S75 type, mounted on the metering arm, and the exit orifice of the solid metering device likewise secured below on the metering arm were aligned in parallel at a distance of 6 cm and, with the aid of an angle-measuring instrument, at an angle of 40° to the horizontal. The powder is metered in outside the spray cone of the nozzle. The nozzle orifice and exit orifice of the solid metering device show a direction of rotation of the drum. The drum rotated clockwise at 15 rpm during the coating.

The coating was effected at 25° C. over a period of 40 min. Thereafter, the coated support materials were dried at air input temperature 130° C. and air output temperature 81° C. for 27 min. Thereafter, they were cooled to 25° C. in the drum at rest over a period of 30 min. During the coating, the powder supplied was for the most part taken up on the surface of the support. The portions which were not taken up were collected in a filter downstream of the drum.

The coated shaped support bodies were treated in an air circulation drying cabinet from Memmert GmbH+Co. KG (UM 400 type; internal volume=53 l; air flow rate=800 l/h), in order to remove the glycerol still present in the sample. For this purpose, the air circulation drying cabinet was heated to 300° C. (including the air temperature) within 2 h and then kept at 300° C. for 2 h. During the drying, the drying material was layered on a perforated sheet positioned in the center of the drying cabinet (the hole diameter of the passage orifices distributed homogeneously over the perforated sheet=0.5 cm; the orifice ratio of the perforated sheet was 60%; the total cross-sectional area of the perforated sheet was 35 cm×26 cm=910 cm$^2$) (bed height=2 cm). Thereafter, the air circulation drying cabinet was cooled to 40 to 50° C. within 2 to 3 h and the sample was removed. The hollow cylindrical eggshell catalysts C1 removed from the air circulation drying cabinet had, based on the total mass thereof, an oxidic eggshell content of 19.9% by weight.

C2 (Example) Berl Saddle 6 mm

Catalyst C2 was shaped as in C1, though in contradistinction to C1, rather than hollow-cylindrical shaped support bodies (7 mm external diameter, 3 mm length, 4 mm internal diameter, C220 steatite) from Ceramtec, 1600 g of Berl saddle bodies (Acidur specialty stoneware, about 70% SiO$_2$, min. 20% Al$_2$O$_3$, 2-3% Fe$_2$O$_3$ and TiO$_2$, 2.5-3.5% K$_2$O and Na$_2$O, 0.5-1% MgO and CaO, material density 2.6 g/cm$^3$, BET surface area <0.1 m$^2$/g) with a characteristic length 6 mm (specific weight: 900 kg/m3, specific surface area 1150 m$^2$/m$^3$, free volume 63%) from Vereinigte Füllkörper-Fabriken GmbH & Co. KG of D-56225 Ransbach-Baumbach, Germany were used. After the air circulation drying cabinet heat treatment carried out as for C1, the coated Berl saddle bodies taken from the air circulation drying cabinet had, based on the total mass thereof, an oxidic eggshell content of 19.8% by weight.

C3 (Example) Berl Saddle 8 mm

Catalyst C3 was shaped as in C1, though in contradistinction to C1, rather than hollow-cylindrical shaped support bodies (7 mm external diameter, 3 mm length, 4 mm internal diameter, C220 steatite) from Ceramtec, 1600 g of Berl saddle bodies (Acidur specialty stoneware, about 70% SiO$_2$, min. 20% Al$_2$O$_3$, 2-3% Fe$_2$O$_3$ and TiO$_2$, 2.5-3.5% K$_2$O and Na$_2$O, 0.5-1% MgO and CaO, material density 2.6 g/cm$^3$, BET surface area <0.1 m$^2$/g) with a characteristic length 8 mm from Vereinigte Füllkörper-Fabriken GmbH & Co. KG of D-56225 Ransbach-Baumbach, Germany were used. After the air circulation drying cabinet heat treatment carried out as for C1, the coated Berl saddle bodies taken from the air circulation drying cabinet had, based on the total mass thereof, an oxidic eggshell content of 19.6% by weight.

Coating of Berl Saddle Bodies in Comparison to the Coating with Hollow-Cylindrical Annular Tablets Twinning refers to the adhesion of two shaped support bodies to one another in the course of coating. Increased twinning leads to an unusable product and therefore to production losses. In the coating of hollow-cylindrical annular tablets, increased twinning was found in 5% of the cases, while in the coating of Berl saddle bodies there were no production losses recorded because of twinning.

II. Gas Phase Oxidation of Acrolein to Acrylic Acid Using a Fixed Catalyst Bed with Two Successive Reaction Zones

EXAMPLE 1

Gas Phase Oxidation of Acrolein to Acrylic Acid

A reaction tube (V2A steel; external diameter 30 mm; wall thickness 2 mm; internal diameter 26 mm; length 464 cm) comprised, from the top downward:
Section 1: length 79 cm, empty tube;
Section 2: length 62 cm, preliminary bed of steatite rings of geometry 7 mm×3 mm×4 mm (external diameter×length× internal diameter; C 220 steatite from CeramTec);
Section 3: length 100 cm, fixed catalyst bed of a homogeneous mixture consisting of 20% by weight of the respective support material used in coating the catalyst and 80% by weight of the respective catalyst;
Section 4: length 200 cm, fixed catalyst bed consisting exclusively of the respective catalyst used in Section 3;
Section 5: length 10 cm, downstream bed of the same steatite rings as in Section 2;
Section 6: length 14 cm, catalyst base made from V2A steel to accommodate the fixed catalyst bed.

A reaction gas mixture was conducted through the respective reaction tube, flowing through the reaction tube from the top downward, which had the following contents on entry into the reaction tube:
4.3% by volume of acrolein,
0.2% by volume of propene,
0.2% by volume of propane,
0.3% by volume of acrylic acid,
5.4% by volume of $O_2$,
7.0% by volume of $H_2O$,
0.4% by volume of CO and $CO_2$,
82.2% by volume of $N_2$.

The space velocity of acrolein on the fixed catalyst bed was in each case 75 l (STP)/(lh).

A stirred and externally electrically heated salt bath (mixture of 53% by weight of potassium nitrate, 40% by weight of sodium nitrite and 7% by weight of sodium nitrate, 50 kg of salt melt) flowed around the reaction tube over its length (apart from the last 10 cm of the empty tube in Section 1 and the last 3 cm of the tube in Section 6) (the flow rate in the tube was 3 m/s (in the plane at right angles to the longitudinal axis of the tube)).

The pressure drop $\Delta p$ (in mbar) corresponds to the difference in the pressure measured at the reactor entry and reactor exit.

The salt bath temperature $T^B$ corresponds to the temperature at which the salt melt was conducted into the salt bath. In all cases, it was set so as to result in an acrolein conversion $C^A$ of 99.3 mol % based on a single pass of the reaction mixture through the fixed catalyst bed. There was no change in the temperature of the salt bath owing to heating along the reaction tube (more heat was emitted by the salt bath than was released to the salt bath by the reaction tube). At the inlet of the reaction tube, the temperature of the reaction gas corresponded to the respective salt bath temperature $T^B$. The highest local temperature $T^H$ was determined by a point measurement in the reaction tube. The results achieved using various catalysts are summarized in Table 2.

The selectivity of acrylic acid formation ($S^{AA}$ (mol %)) is understood in this document to mean:

$$S^{AA} = \frac{\text{number of moles of acrolein converted to acrylic acid}}{\text{number of moles of acrolein converted overall}} \times 100.$$

(the conversion figures are based in each case on a single pass of the reaction gas mixture through the fixed catalyst bed).

Table 1 below shows the outcomes resulting as a function of the eggshell catalyst used after 100 hours of operation in each case:

TABLE 1

| Example | $\Delta p$ [1] [mbar] | $T^B$ [2] [° C.] | $S^{AA}$ [1] [mol %] |
|---------|---------|---------|---------|
| C1*  | 170 | 259 | 97.2 |
| C2   | 120 | 263 | 97.5 |
| C3   | 120 | 266 | 97.5 |

*noninventive
[1] reactor pressure drop;
[2] salt bath temperature;
[3] selectivity of acrylic acid formation In the case of the inventive catalysts, the selectivity of acrylic acid formation, at 97.5 mol %, is significantly higher than in the case of the noninventive catalyst C1.

EXAMPLE 2

Gas Phase Oxidation of Acrolein to Acrylic Acid Using a Fixed Catalyst Bed with Two Successive Reaction Zones Charged with Inventive and Noninventive Eggshell Catalysts A reaction tube (stainless steel type 1.4541 (EU standard number EN 10088-3); external diameter 33.7 mm; wall thickness 2 mm; internal diameter 29.7 mm; length 400 cm, thermowell 4 mm) was charged as follows from the bottom upward:
Section 1: length 70 cm
  Upstream bed of steatite rings of geometry 7 mm×3 mm×4 mm (external diameter×length×internal diameter; C220 steatite from CeramTec);
Section 2: length 100 cm
  Fixed catalyst bed of a homogeneous mixture consisting of 30% by weight of the respective support material used in the coating of the catalyst and 80% by weight of the respective catalyst; 70% by weight of the respective eggshell catalyst;
Section 3: length 200 cm
  Fixed catalyst bed of the respective eggshell catalyst;
Section 4: length 8 cm
  Downstream bed of the same steatite rings as in Section 1;
Section 5: length 23 cm
  Empty tube The reaction tube was operated under two different sets of reaction conditions, differing in the composition of the reaction gas mixture, the space velocity of acrolein on the fixed catalyst bed (as defined in DE-A 19927624), and the pressure set and regulated at the reactor exit. A reaction gas mixture was conducted through the respective reaction tube charged as described above, flowing through the reaction tube from the top downward, which had the following contents:

TABLE 2

|  |  | Reaction conditions | |
|---|---|---|---|
| Gas composition |  | 1 | 2 |
| Acrolein | vol % | 4.5 | 5.1 |
| Propene | vol % | 0.1 | 0.2 |
| Propane | vol % | 0.07 | 0.07 |
| Acrylic acid | vol % | 0.5 | 0.8 |
| $O_2$ | vol % | 5.4 | 5.8 |
| $H_2O$ | vol % | 7 | 8 |
| CO and $CO_2$ | vol % | 1.6 | 1.6 |
| Remainder |  | $N_2$ | $N_2$ |
| Space velocity of acrolein on the fixed catalyst bed | ($h^{-1}$) | 75 | 103 |
| Pressure at reactor exit | (bar g) | 0.42 | 0.62 |

A stirred and externally electrically heated salt bath (mixture of 53% by weight of potassium nitrate, 40% by weight of sodium nitrite and 7% by weight of sodium nitrate; 50 kg of salt melt) flowed around the reaction tube over its length (the flow rate in the tube was 3 m³/h (in the plane at right angles to the longitudinal axis of the tube)).

The salt bath temperature $T^B$ (° C.) (with which the salt bath was supplied) was adjusted in all cases so as to result in an acrolein conversion, based on a single pass of the reaction gas mixture through the fixed catalyst bed, of 99.3 mol %. There was no change in the salt bath temperature along the reaction tube owing to heating (more heat was emitted by the salt bath than was released from the reaction tube to the salt bath). The feed temperature of the reaction gas mixture (at the inlet into the reaction tube) was adjusted in each case to the respective salt bath temperature.

The temperature in the catalyst bed was measured continuously by means of a thermocouple which had been positioned in a thermowell within the interior of the reactor tube and which had been moved from the bottom upward within the reactor bed with the aid of a pulling machine. The maximum temperature in this measurement corresponded to the hotspot temperature $T^H$.

The table below shows the outcomes resulting after 100 hours of operation, which are established after charging reactor sections 2 and 3 with different inventive and noninventive eggshell catalysts.

TABLE 3

| Catalyst | Reaction conditions | $\Delta p$ [bar] | $T^B$ [° C.] | $T^H$ [° C.] | $S^{AA}$ [mol %] |
|---|---|---|---|---|---|
| C1* | 1 | 0.17 | 264 | 313 | 97.4 |
| C2 | 1 | 0.14 | 267 | 310 | 98.0 |
| C1* | 2 | 0.23 | 266 | 331 | 97.1 |
| C2 | 2 | 0.16 | 269 | 313 | 97.8 |

*noninventive
1) reactor pressure drop;
2) salt bath temperature;
3) hotspot temperature;
4) selectivity of acrylic acid formation The comparison of the acrylic acid selectivity $S^{AA}$ of the inventive catalyst C2 (98.0 and 97.8 mol %) in comparison to the reference (97.1 and 97.4 mol %) shows that saddle shaped bodies as catalyst supports are advantageous in respect of the selectivity of acrylic acid formation. Furthermore, the pressure drop in the reactor when using the saddle shaped bodies of the invention is much lower than when using the hollow-cylindrical shaped support bodies.

EXAMPLE 3

The pressure drop for the catalyst beds was determined additionally. The results are summarized in Table 4:

TABLE 4

| Example | | Geometric surface area/piece mm²/piece | Number of shaped bodies for 20 cm bed length in tube di = 26 mm | Weight of 100 pieces in grams | Bulk density in tube with di = 26 mm in g/cm³ | Geometric packing surface area/m of bed in 26 mm tube in m²/m | Specific surface area based on ring without internal surface | Measurement values Pressure drop (mbar/m) | Bulk density in tube with di = 26 mm in g/cm³ |
|---|---|---|---|---|---|---|---|---|---|
| C2 | Berl saddles 6 mm | 223 | 262 | 26 | 0.642 | 0.292 | 1.09 | 22.4 | 0.747 |
| C3 | Berl saddles 8 mm | 379 | 110 | 66 | 0.684 | 0.209 | 0.78 | 13.2 | 0.733 |
| C1 | Ring 7 × 3 × 4 with internal surface | 156 | 455 | 19 | 0.814 | 0.354 | 1.32 | 41.0 | 0.966 |

The inventive catalysts lead to a significantly reduced pressure drop in the application

The invention claimed is:

1. An oxidation catalyst comprising at least one inorganic, oxidic or ceramic, shaped support body having a BET surface area of less than 0.5 m²/g, based on the support, which is at least partly coated with a catalytically active multielement oxide, the catalyst being precious metal-free and the shaped support body having the form of a saddle whose saddle surface is curved oppositely in the two principal directions,
wherein the multielement oxide composition conforms to the general formula (I)

$$Mo_{12}V_aX^1_bX^2_cX^3_dX^4_eX^5_fO_n \qquad (I),$$

in which
$X^1$ is W, Nb, Ta, Cr and/or Ce,
$X^2$ is Cu, Ni, Co, Fe, Mn and/or Zn,
$X^3$ is Sb and/or Bi, X⁴ is one or more alkali metals and/or alkaline earth metals and/or N,
X⁵ is Si, Al, Ti and/or Zr,
a is a number in the range from 1 to 6,
b is a number in the range from 0.2 to 4,
c is a number in the range from 0 to 18,
d is a number in the range from 0 to 40,
e is a number in the range from 0 to 4,
f is a number in the range from 0 to 40, and
n is the stoichiometric coefficient of the element oxygen, which is determined by the stoichiometric coefficients of the elements other than oxygen and by their charge number in (I).

2. The oxidation catalyst according to claim 1, wherein the catalyst is free from metals with oxidation state zero.

3. The oxidation catalyst according to claim 1, wherein the shaped catalyst body is designed as Intalox or Berl saddles.

4. The oxidation catalyst according to claim 1, wherein the shaped support body in the form of a saddle has one or more ribs on the saddle surface.

5. The oxidation catalyst according to claim 1, wherein the maximum extent of the shaped support body is 20 mm.

6. The oxidation catalyst according to claim 1, wherein the amount of multielement oxide, based on the overall oxidation catalyst, is 2 to 50 wt %.

7. The oxidation catalyst according to claim 1, wherein the molar proportion of the element Mo in the total amount of all elements other than oxygen in the multielement oxide composition (I) is 20 mol % to 80 mol %.

8. The oxidation catalyst according to claim 1, wherein the molar ratio of Mo present in the catalytically active multielement oxide composition (I) to V present in the catalytically active multielement oxide composition (I), Mo/V, is 15:1 to 1:1.

9. The oxidation catalyst according to claim 1, wherein the multielement oxide composition comprises Nb and the molar ratio Mo/(total amount of \V and Nb) is 80:1 to 1:4.

10. The oxidation catalyst according to claim 1, wherein the multielement oxide composition comprises Cu and the molar ratio Mo/Cu is 30:1 to 1:3.

11. A process for producing an oxide catalyst according to claim 1, wherein the inorganic oxidic or ceramic support is coated with a powder of the multielement oxide, optionally with accompanying use of a binder.

12. A process for preparing an α,β-unsaturated carboxylic acid by gas phase oxidation of an α,β-unsaturated aldehyde with molecular oxygen over a fixed catalyst bed which comprises a bed of a catalyst according to claim 1.

13. A process for oxidatively dehydrogenating n-butenes to butadiene, in which an initial gas mixture comprising n-butenes is contacted with an oxygen-comprising gas, optionally mixed with additional inert gas or water vapor, in a fixed bed reactor at a temperature of 220 to 490° C. with a catalyst according to claim 1 arranged in a fixed catalyst bed.

* * * * *